United States Patent
Motai

(10) Patent No.: US 10,595,859 B2
(45) Date of Patent: Mar. 24, 2020

(54) SUTURE MEMBER

(71) Applicant: OLYMPUS CORPORATION, Hachioji-shi, Tokyo (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 248 days.

(21) Appl. No.: 15/896,527

(22) Filed: Feb. 14, 2018

(65) Prior Publication Data

US 2018/0168571 A1 Jun. 21, 2018

Related U.S. Application Data

(63) Continuation of application No. PCT/JP2016/064102, filed on May 12, 2016.

(30) Foreign Application Priority Data

Aug. 18, 2015 (JP) .................................. 2015-161082

(51) Int. Cl.
*A61B 17/06* (2006.01)
*A61B 17/04* (2006.01)
(Continued)

(52) U.S. Cl.
CPC .... *A61B 17/06004* (2013.01); *A61B 17/0485* (2013.01); *A61B 17/06066* (2013.01);
(Continued)

(58) Field of Classification Search
CPC . A61B 17/04; A61B 17/0483; A61B 17/0487; A61B 17/06; A61B 17/06004;
(Continued)

(56) References Cited

U.S. PATENT DOCUMENTS 5,178,629 A 1/1993 Kammerer
2012/0245629 A1* 9/2012 Gross ............... A61B 17/06166
606/228

(Continued)

FOREIGN PATENT DOCUMENTS

JP H06-007422 A 1/1994
JP H10-337291 A 12/1998
(Continued)

OTHER PUBLICATIONS

Jul. 12, 2016 Search Report issued in International Patent Application No. PCT/JP2016/064102.

*Primary Examiner* — Tuan V Nguyen
(74) *Attorney, Agent, or Firm* — Oliff PLC

(57) ABSTRACT

A suture member includes: a suture needle of which a distal end is sharp; a suture thread which includes a first end portion and a second end portion, of which the first end portion is connected to the suture needle, and which sutures the tissue; a first loop portion which has a ring shape, through which the suture needle is capable of passing, and which is connected to the second end portion; and a second loop portion which has a ring shape, through which the suture needle is capable of passing, which is connected to the second end portion, and which is provided to separate from the first loop.

5 Claims, 16 Drawing Sheets

(51) Int. Cl.
    *A61B 17/12*     (2006.01)
    *A61B 17/062*    (2006.01)
(52) U.S. Cl.
    CPC .. *A61B 17/06166* (2013.01); *A61B 17/12009* (2013.01); *A61B 17/0401* (2013.01); *A61B 17/062* (2013.01)
(58) Field of Classification Search
    CPC .......... A61B 17/0485; A61B 17/06066; A61B 17/06166; A61B 17/12009; A61B 2017/06176; A61B 2017/06185; A61B 2017/06171
    See application file for complete search history.

(56)  References Cited

U.S. PATENT DOCUMENTS

| | | | |
|---|---|---|---|
| 2013/0226233 A1* | 8/2013 | D'Agostino | A61B 17/04 606/228 |
| 2014/0257027 A1 | 9/2014 | Palmisano et al. | |

FOREIGN PATENT DOCUMENTS

| | | |
|---|---|---|
| JP | 2008-543509 A | 12/2008 |
| WO | 2007/002561 A1 | 1/2007 |

* cited by examiner

SUTURE MEMBER

TECHNICAL FIELD

The present invention relates to a suture member.

This application is a continuation application based on a PCT Patent Application No. PCT/JP2016/064102, filed on May 12, 2016, whose priority is claimed on Japanese Patent Application No. 2015-161082, filed in Japan on Aug. 18, 2015. The contents of both the PCT Application and the Japanese Application are incorporated herein by reference.

BACKGROUND ART

Conventionally, a suture member is suggested in which a tissue is sutured using a suture needle and a suture thread. One end of the suture thread is connected to the suture needle and a loop portion is provided in the other end of the suture thread. However, when the suture needle is passed through the loop portion and is just pulled, there is a possibility of the suture thread being loosened. To solve this problem, a surgical suture needle that provides a clip at the loop portion has been suggested (for example, Japanese Unexamined Patent Application, First Publication No. H10-337291).

In the surgical suture needle of the Japanese Unexamined Patent Application, First Publication No. H10-337291, the clip provided in the loop portion is attached so as to be slidable with respect to the thread of the loop portion. When the suture of the tissue is performed using this surgical suture needle, the needle is passed through the loop portion and is pulled after the needle is penetrated through the body tissue to be sutured. Therefore, the loop portion gradually becomes smaller and the body tissue is bound by the suture thread. The end portion of the suture thread is pinched in the clip and the clip is deformed by being crushed. As a result, it is possible to prevent the suture thread from loosening by fixing the suture thread in the clip.

SUMMARY OF INVENTION

According to a first aspect of the present invention, a suture member that suture a tissue includes: a suture needle of which a distal end is sharp; a suture thread which includes a first end portion and a second end portion, of which the first end portion is connected to the suture needle, and which sutures the tissue; a first loop portion which has a ring shape, through which the suture needle is capable of passing, and which is connected to the second end portion; a second loop portion which has a ring shape, through which the suture needle is capable of passing, which is connected to the second end portion, and which is separated from the first loop; a first straight portion which is provided between the second end portion and the first loop portion; and a second straight portion which is provided between the second end portion and the second loop portion.

According to a second aspect of the present invention, in the suture member of the first aspect, a sum of a length of the first straight portion and a maximum length of the first loop portion in a longitudinal direction of the first straight portion may be larger than a sum of a length of the second straight portion and a maximum length of the second loop portion in a longitudinal direction of the second straight portion.

According to a third aspect of the present invention, in the suture member of the first aspect, a stopper that prevents the first loop portion and the second loop portion from being buried in the tissue may be provided to the second end portion.

According to a fourth aspect of the present invention, in the suture member of the first aspect, a visible marker may be provided in the second end portion.

According to a fifth aspect of the present invention, a method for suturing a first tissue and a second tissue by a suture device using the suture member according to the first aspect, the method includes: causing the suture needle to penetrate from the first tissue through the second tissue and protruding the suture needle and the suture thread from the second tissue side; passing the suture needle through the first loop portion from a back side thereof twice, and entangling the suture thread in the first loop portion by manipulating the suture device; pulling the suture needle toward a direction away from the first tissue and the second tissue, and tightening the suture thread; making a loop by intersecting the suture thread passing through the second loop portion with the suture thread extending from the first loop portion toward the second loop portion in the back side of the suture thread extending from the first loop portion toward the second loop portion; passing the suture needle through the loop from a front side of the loop once by manipulating the suture device; and pulling the suture needle toward a direction away from the first tissue and the second tissue, and tightening the suture thread.

DESCRIPTION OF EMBODIMENTS

First Embodiment

A suture member according to a first embodiment of the present invention will be described with reference to FIGS. 1 to 15.

Figure 1:
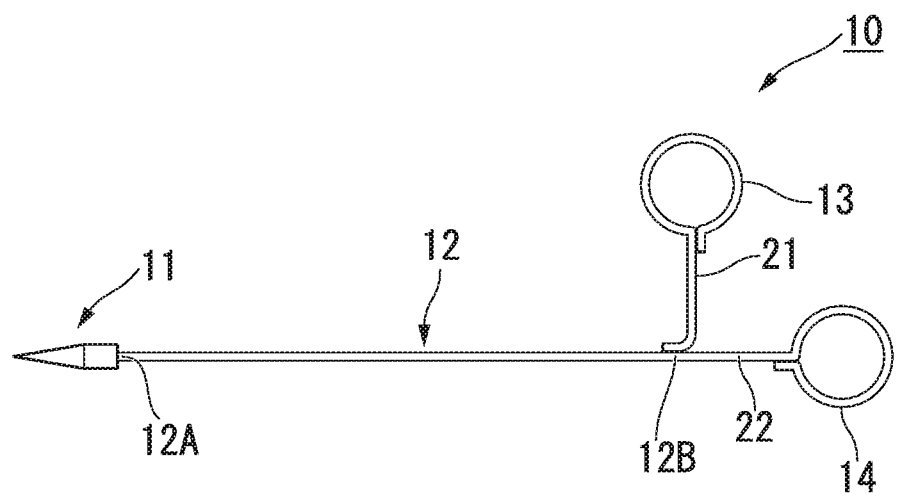
FIG. 1 is an overall view showing a suture member of a first embodiment of the present invention.

The suture member 10 according to the present invention, as shown in FIG. 1, includes a suture needle 11 which has a nearly straight shape and of which a distal end is sharp, a suture thread 12 that sutures a tissue, a first loop portion 13 that has a loop shape or a ring shape, and a second loop portion 14 that has a loop shape or a ring shape and that is provided to separate from the first loop. The first loop portion 13 and the second loop portion 14 have an internal diameter through which the suture needle 11 is capable of passing.

The suture thread 12 includes a first end portion 12A and a second end portion 12B. The suture needle 11 is connected to the first end portion 12A of the suture thread 12.

The suture member 10 further includes a first straight portion 21 that is provided between the second end portion 12B and the first loop portion 13, and a second straight portion 22 that is provided between the second end portion 12B and the second loop portion 14. That is, the second end portion 12B is a branching point at which the suture thread 12 is divided into the first straight portion 21 and the second straight portion 22.

In this embodiment, the suture thread 12 and the second straight portion 22 are formed integrally, and the first straight portion 21 is fixed to the second end portion 12B with an adhesive. An end of the first loop portion 13 is fixed to the first straight portion 21 with an adhesive, and a termination of the first loop portion 14 is fixed to the second straight portion 22 with an adhesive. The adhesive is preferably one of the group consisting of polypropylene resin, polypropylene resin, and biocompatible resin.

Figure 2:
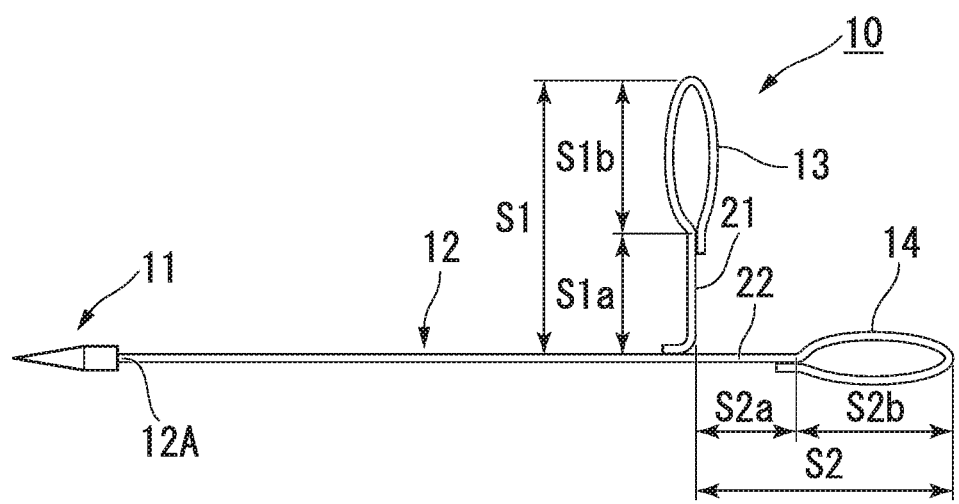
FIG. 2 is a view showing a maximum length of a loop portion of FIG. 1.

As shown in FIG. 2, a sum S1 (S1a+S1b) of a length S1a of the first straight portion 21 and a maximum length S1b of the first loop portion 13 in a longitudinal direction of the first straight portion 21 is larger than a sum S2 (S2a+S2b) of a length S2a of the second straight portion 22 and a maximum length S2b of the second loop portion 14 in a longitudinal direction of the second straight portion 22.

Next, a suture device that sutures the tissue using the above-mentioned the suture member 10 will be described.

Figure 3:
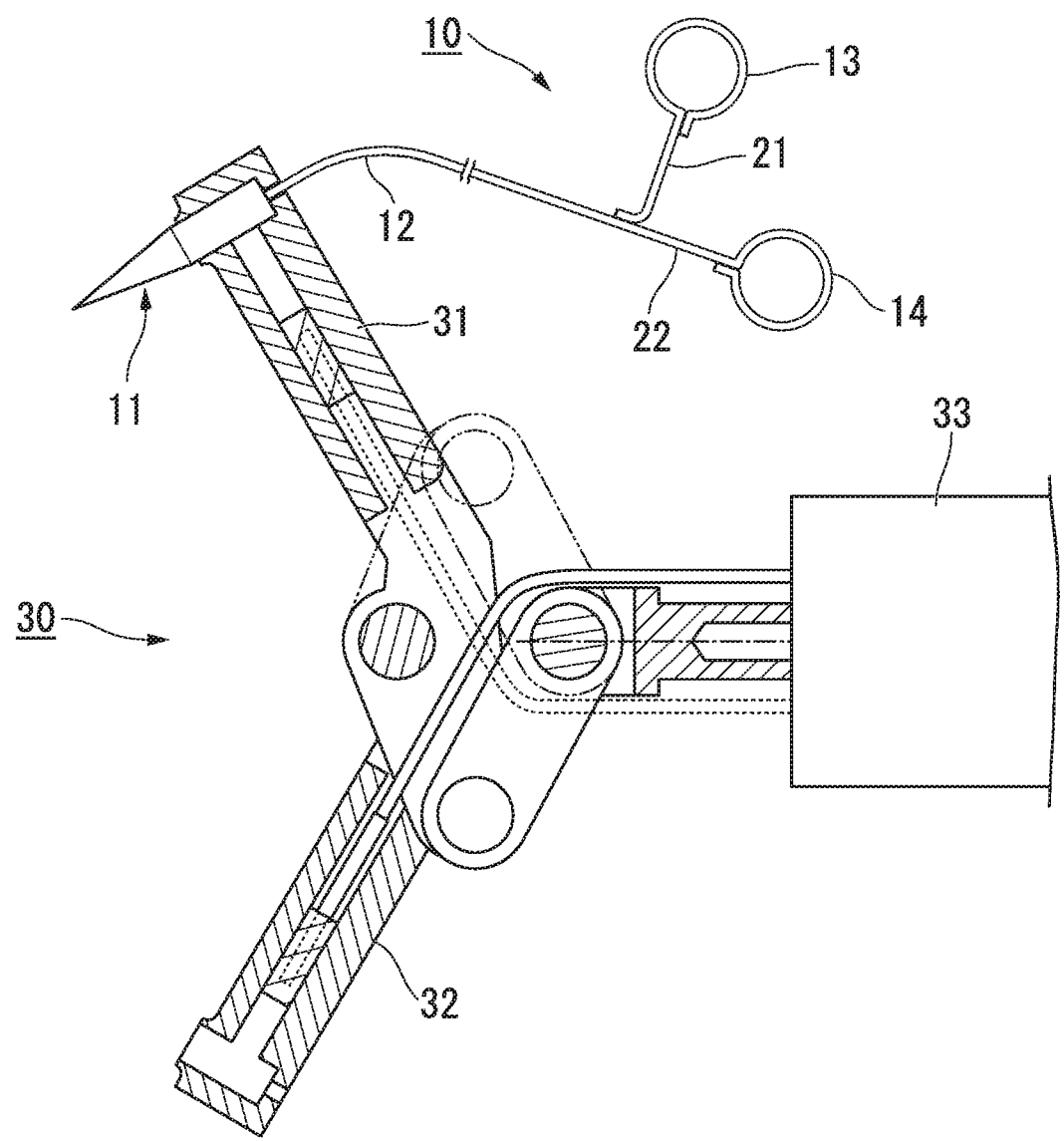
FIG. 3 is a view showing a suture device used for the first embodiment of the present invention.

The suture device to be used is not limited; for example, a suture device 30 shown in FIG. 3 includes a first grasping member 31, a second grasping member 32, a longitudinal member 33, and a manipulation part (not shown).

The first grasping member 31 and the second grasping member 32 are provided at a distal end of the longitudinal member 33. The above-mentioned suture member 10 is capable of engaging to the first grasping member 31 and the second grasping member 32.

The longitudinal member 33 extends from a proximal end side of the first grasping member 31 and the second grasping member 32, and is connected to the manipulation part. The manipulation part is capable of opening and closing the first grasping member 31 and the second grasping member 32, and is capable of deliver the suture needle 11 of the suture member 10 from the first grasping member 31 side to the second grasping member 32 side.

Next, a method for suturing the tissue by the suture device using the suture member will be described.

In the below description, the suture device is omitted as needed in order to simplifying the drawings when the procedure of a way of knotting using the suture thread 12 is described.

First, the suture needle 11 of the suture member 10 is engaged to the first grasping member 31 and the second grasping member 32, and the first grasping member 31 and the second grasping member 32 are hold in a state of closing. An endoscope is penetrated through a body cavity by a well-known technique, a distal end of the endoscope is guided to a target to be treated, and the target to be sutured is caught in a field of the endoscope (not shown). The suture device 30 is protruded from the distal end of the endoscope.

Figure 4:
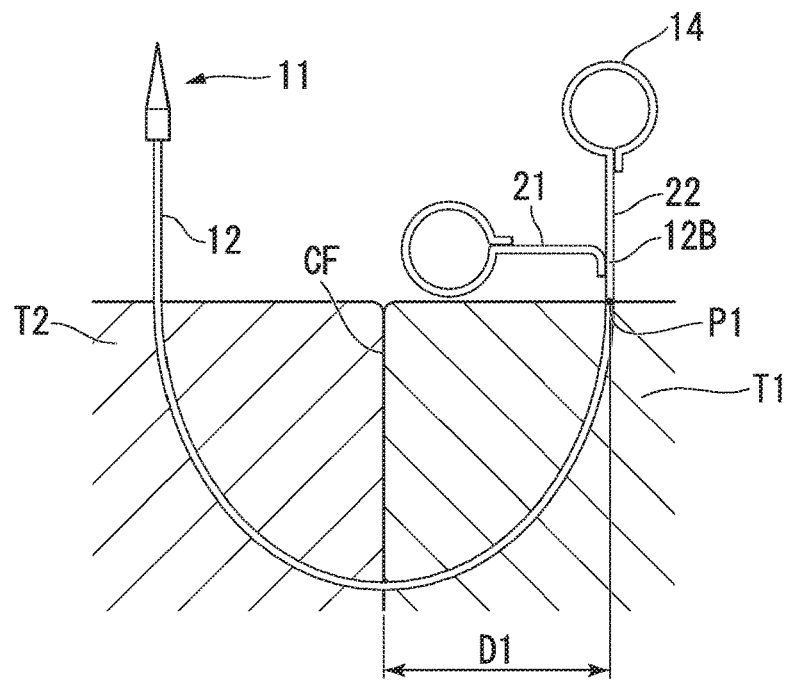
FIG. 4 is a view showing a method for suturing a tissue using the suture member of FIG. 1.

An operator causes the distal end of the suture device 30 to approach the target (perforation portion) in which the suture treatment is performed. The operator operates the manipulation part and the manipulation part causes the first grasping member 31 and the second grasping member 32 to contact to the target tissue in a state of opening the first grasping member 31 and the second grasping member 32. After that, the operator closes the first grasping member 31 and the second grasping member 32. Therefore, the tissue is grasped between the first grasping member 31 and the second grasping member 32. The operator causes the suture needle 11 of the suture member 10 to penetrate from a first tissue T1 through a second tissue T2 by manipulating the manipulation part, as shown in FIG. 4, the suture needle 11 and the suture thread 12 are protruded from the second tissue T2 side (step ST1). In this time, in the first tissue T1 side, the first loop portion 13 and the second loop portion 14 do not enter into the first tissue T1 and expose.

When the first tissue T1 and the second tissue T2 are grasped, an piercing point at which the suture needle 11 is punctured is defined as P1, a distance D1 from a contact face CF on which the first tissue T1 and the second tissue T2 are jointed to the piercing point P1 is longer than the length S1. Therefore, the first loop portion 13 does not exceed the contact face CF and is positioned at the first tissue T1 side.

Figure 5:
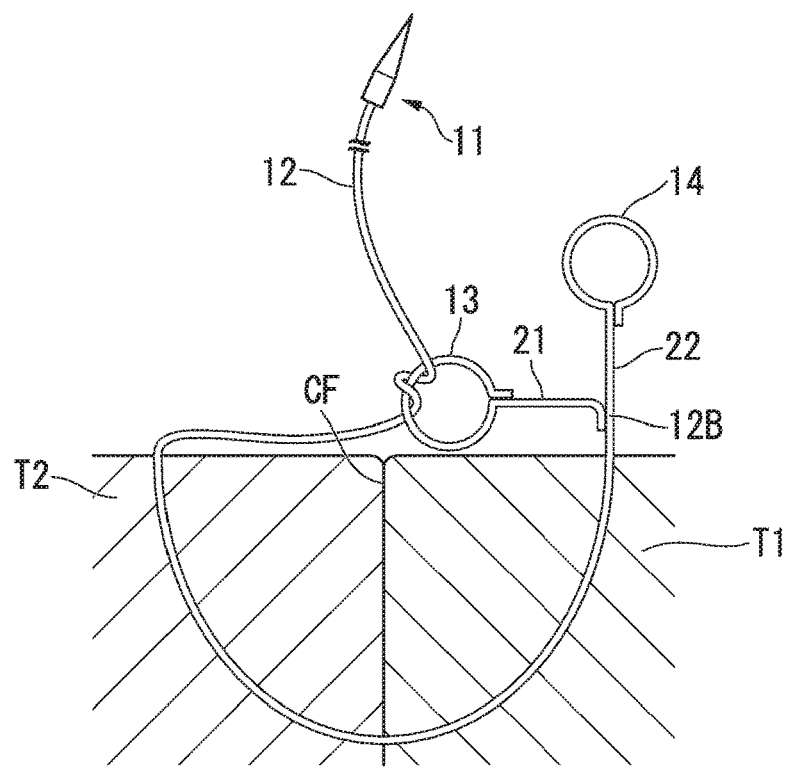
FIG. 5 is a view showing a method for suturing the tissue using the suture member of FIG. 1.

Next, as shown in FIG. 5, the operator manipulates the first grasping member 31 and the second grasping member 32 (not shown), passes the suture needle 11 through the first loop portion 13 from a back side of the first loop portion 13 twice, and causes the suture thread 12 to be entangled in the first loop portion 13. Therefore, the suture thread is a state of a half knot (step ST2).

Figure 6:
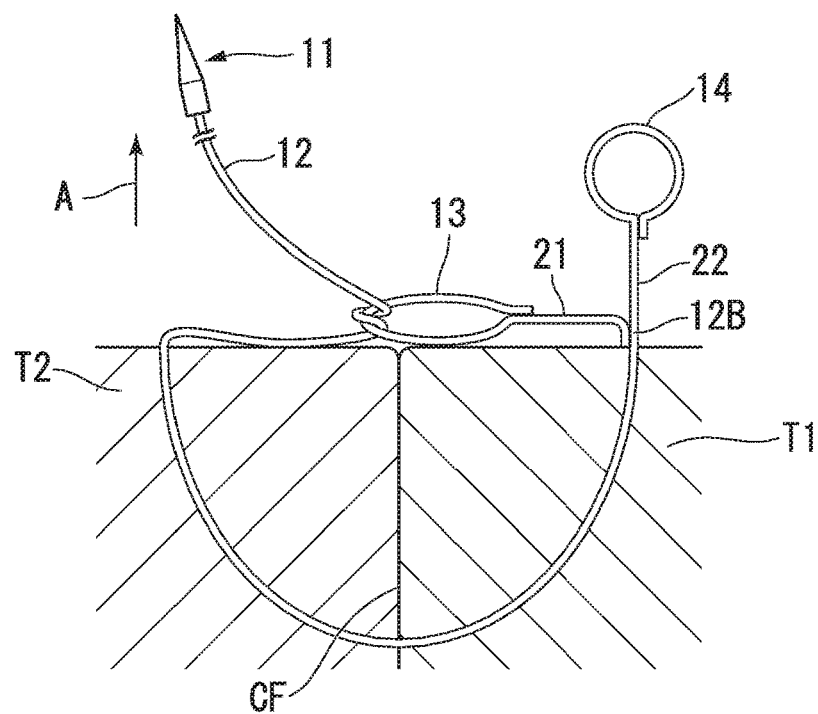
FIG. 6 is a view showing a method for suturing the tissue using the suture member of FIG. 1.
Figure 7:
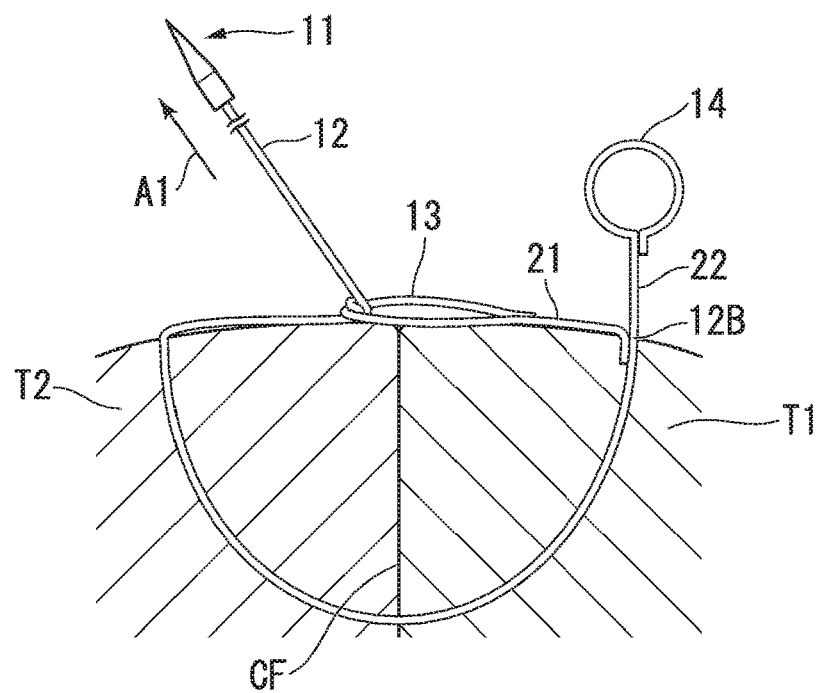
FIG. 7 is a view showing a method for suturing the tissue using the suture member of FIG. 1.

Next, as shown in FIG. 6, the operator pulls the suture needle 11 toward a direction (arrow A direction) away from the tissue and tightens the suture thread 12. Therefore, the first loop portion 13 exceeds the contact face CF and moves to the second tissue T2 side (step ST3). As shown in FIG. 7, the operator pulls the suture needle 11 toward the arrow A direction (obliquely upside with respect to tissues T1, T2), therefore the suture thread 12 is tightened. As a result, the first tissue T1 and the second tissue T2 are closely attached and the second end portion 12B is moved in the first tissue T1.

Intervals are provided between sections of thread so as to clarify the way of knotting in the below description. However, the threads are actually closely attached.

Figure 8:
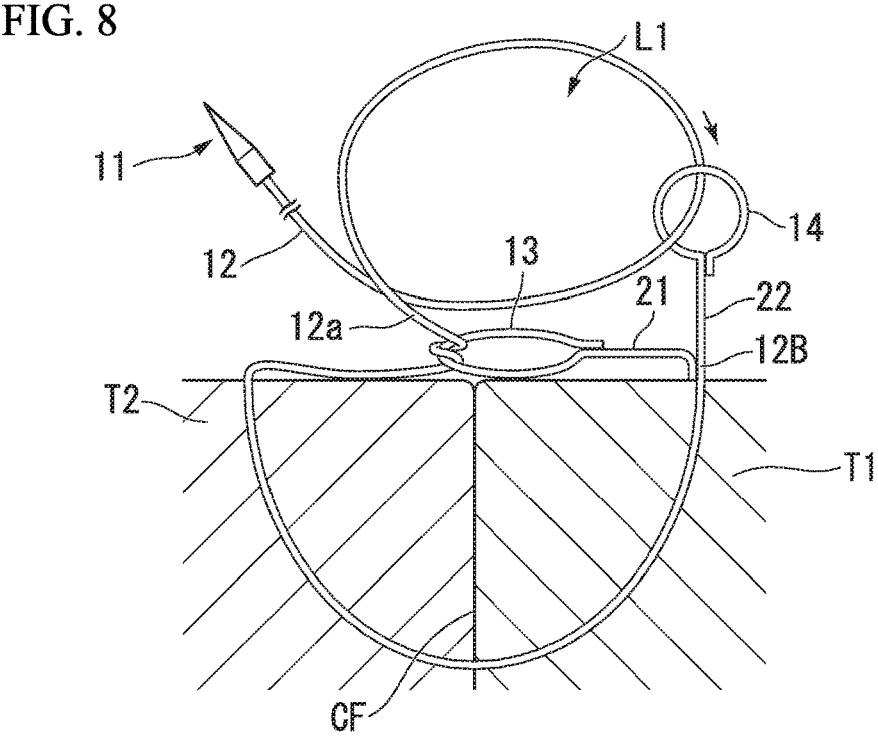
FIG. 8 is a view showing a method for suturing the tissue using the suture member of FIG. 1.

Next, as shown in FIG. 8, the operator manipulates the first grasping member 31 and the second grasping member 32 (not shown), passes the suture needle 11 through the second loop portion 14 from the back side of the second loop portion 14 once, and makes a loop L1 by intersecting the suture thread 12 passing through the second loop portion 14 with the suture thread 12a extending from the first loop portion 13 toward the second loop portion 14 in the back side of the suture thread 12a (step ST4).

Figure 9:
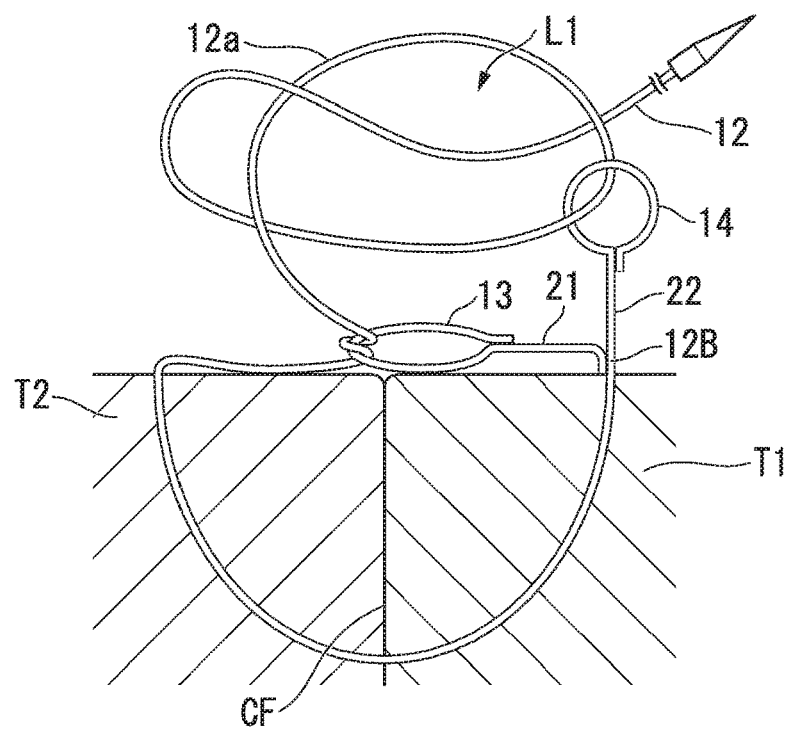
FIG. 9 is a view showing a method for suturing the tissue using the suture member of FIG. 1.

Next, as shown in FIG. 9, the operator manipulates the first grasping member 31 and the second grasping member 32 (not shown), and passes the suture needle 11 through the loop L1 from a front side (a direction opposite to a direction in which the suture thread 12 is passed through the second loop portion 14) of the loop L1 once (step ST5).

Figure 10:
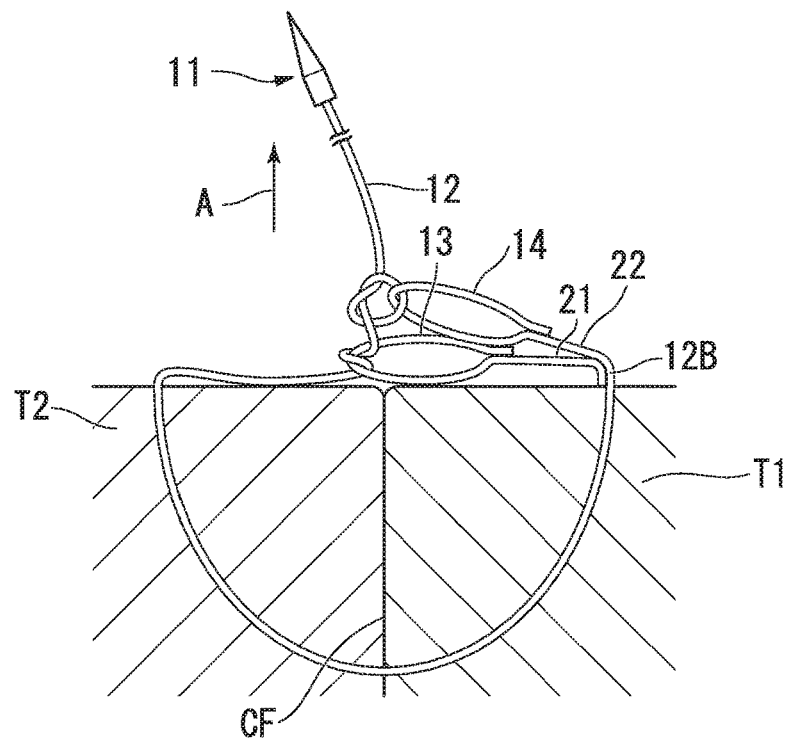
FIG. 10 is a view showing a method for suturing a tissue using the suture member of FIG. 1.
Figure 11:
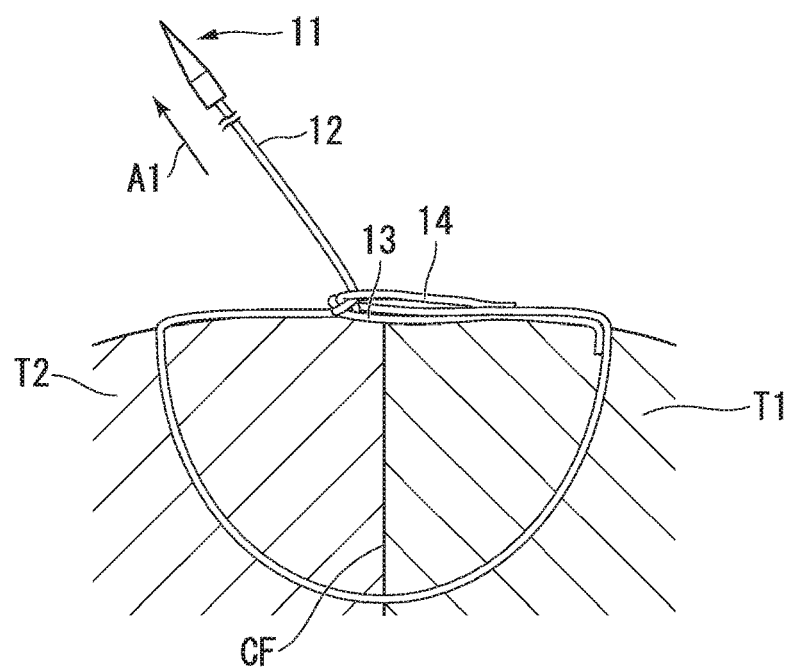
FIG. 11 is a view showing a method for suturing the tissue using the suture member of FIG. 1.

Next, as shown in FIG. 10, the operator pulls the suture needle 11 toward a direction (the arrow A direction) away from the tissue, and tightens the suture thread 12 (step ST6). Therefore, the second loop portion 14 also exceeds the contact face CF and is closely attached to the first loop portion 13. As shown in FIG. 11, the suture thread 12 is tightened by pulling the suture needle 11 toward an arrow A1 direction (obliquely upside with respect to tissues T1, T2) and a surgical knot is completed.

Figure 12:
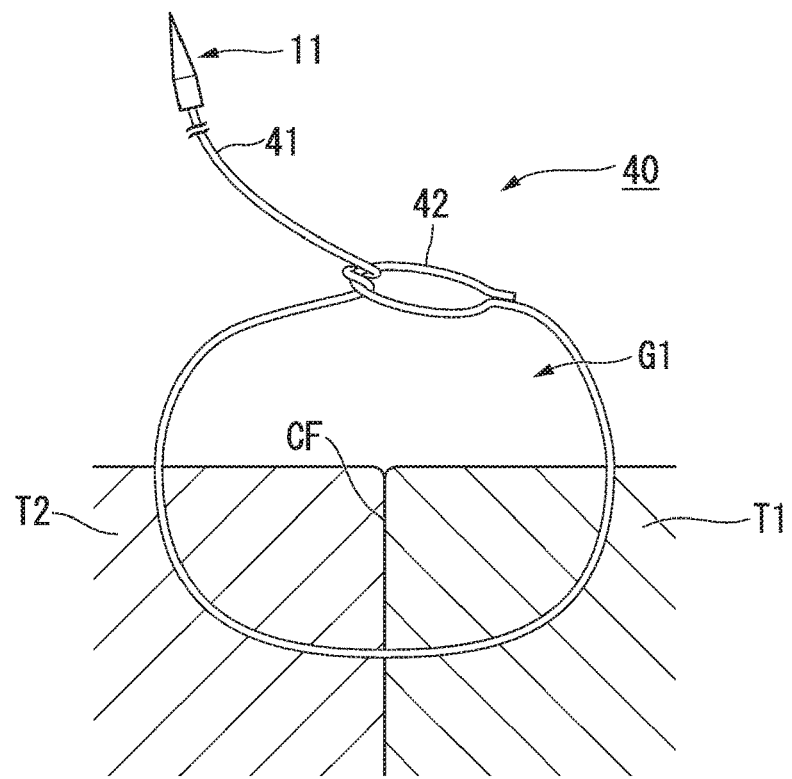
FIG. 12 is a view showing a method for suturing a tissue using the conventional suture member.

On the other hand, a conventional suture member 40, as shown in FIG. 12, includes a suture thread 41 and one loop portion 42.

As with the above-mentioned step ST1 and the step ST2, using the suture device, the operator causes the suture thread 41 to be entangled in the loop portion 42, after the operator causes the suture needle 11 of the suture member 40 to penetrate through the second tissue T2 from the first tissue T1. In this time, in order to inset the suture needle 11 in a next step, it is necessary to provide a gap G1 between the tissues T1, T2 and the loop portion 42.

Figure 13:
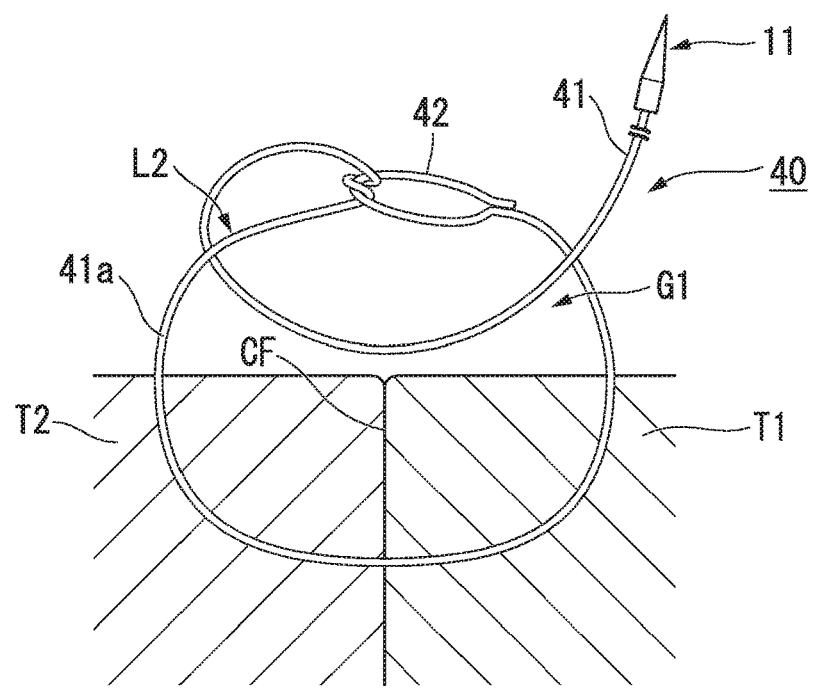
FIG. 13 is a view showing a method for suturing the tissue using the conventional suture member.
Figure 14:
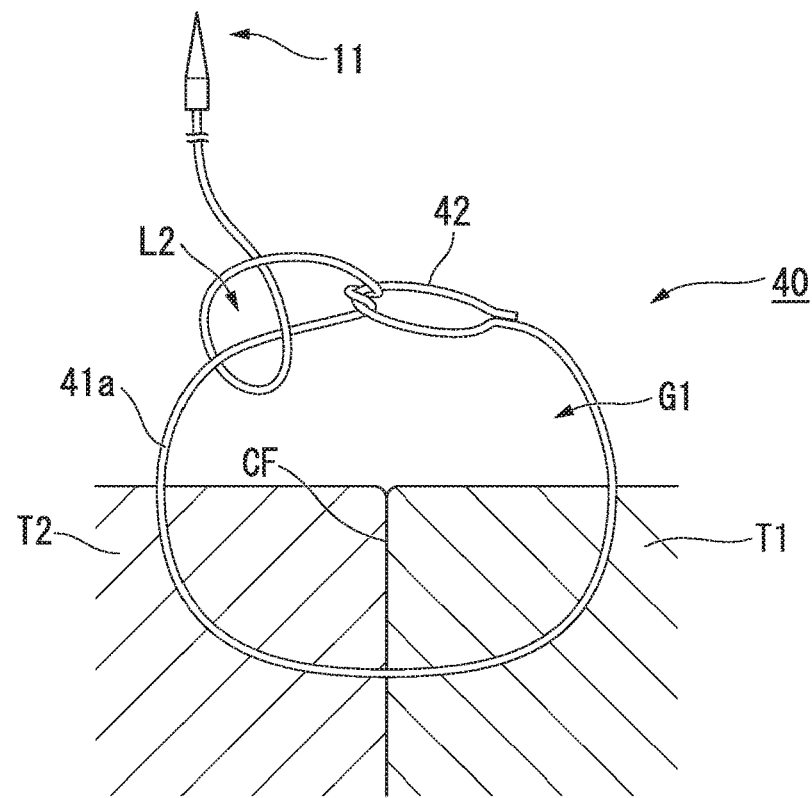
FIG. 14 is a view showing a method for suturing the tissue using the conventional suture member.

Next, as shown in FIG. 13, the operator makes a loop L2 by intersecting the suture thread 41 passing through the loop portion 42 with the suture thread 41a toward the loop portion 42 in the back side of the suture thread 41a toward the loop portion 42 and passes the suture thread 41 through the gap G1 from the back side of the gap G1.

Figure 15:
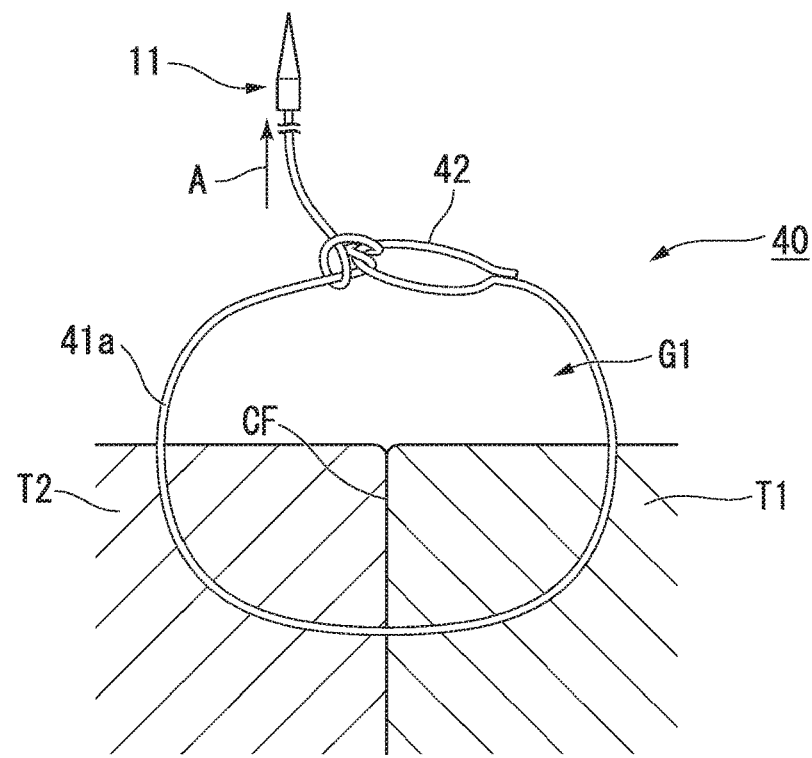
FIG. 15 is a view showing a method for suturing the tissue using the conventional suture member.

Next, the operator passes the suture thread 41 though the loop L2 from the front side (see FIG. 14), pulls the suture thread 41 toward a direction (the arrow A direction) away from the tissue, and tightens the suture thread 41 (see FIG. 15).

As mentioned above, in the conventional suture member 40, in order to perform the surgical knot, because it is necessary to provide the gap G1, the gap G1 eventually remains after tightening the suture thread 41. Therefore, the first tissue T1 and the second tissue T2 cannot be tightened. As a result, the suture thread 41 is loosened.

The tissues can be easily sutured using the treatment tool such as the suture device 30 introduced via the endoscope, because the suture member 10 of the present invention includes the first loop portion 13 and a second loop portion 14 that is provided away from the first loop portion 13. Furthermore, although the gap G1 is provided in the conventional suture member, it is not necessary to provide the gap G1 in the present invention. Therefore, the suture thread 12 is hard to loosen.

Furthermore, it is easy to make a knot at a vicinity of the contact face CF in which the first tissue T1 and the second tissue T2 are joined because the suture member 10 has the first straight portion 21 and the second straight portion 22.

Additionally, in the beginning, although the operator passes the suture thread 12 through the first loop portion 13 twice, because the length S1 is longer than the length S2, the operator can easily pass the suture thread 12 through the first loop portion 13.

The distance D1 from the contact face CF to the piercing point P1 is longer than the length S1, when the first tissue T1 and the second tissue T2 are tightened, the first loop portion 13 moves on the contact face CF or to the second tissue T2 side over the contact face CF by applying the tension toward the arrow A direction. Therefore, it is possible to apply a desired tension to the first tissue T1 and the second tissue T2.

Figure 16:
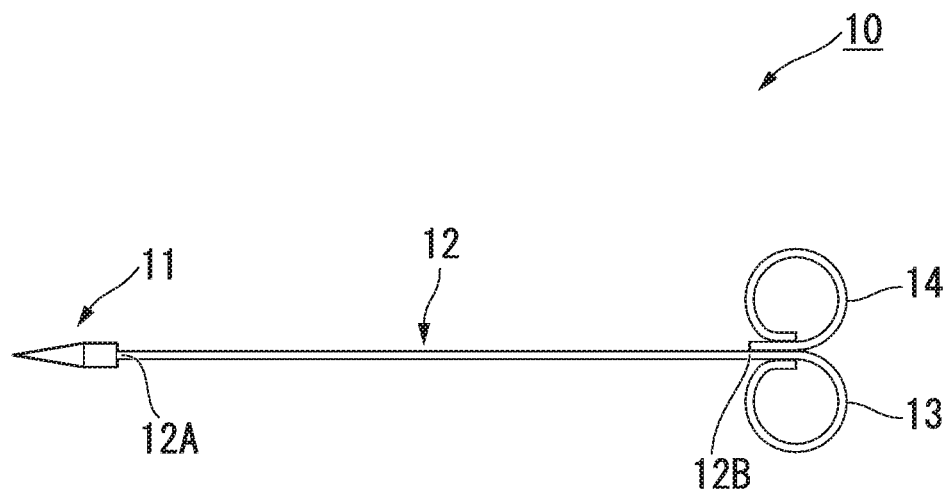
FIG. 16 is an overall view showing a modified example of the suture member of a first embodiment of the present invention.

In the present invention, the first straight portion 21 and the second straight portion 22 may be not provided. For example, as shown in FIG. 16, the first loop portion 13 and the second loop portion 14 that is separated from the first loop portion 13 are directly provided in the second end portion 12B In the present invention, although the suture thread 12 and the second straight portion 22 are formed integrally and the first straight portion 21 is adhered to the second end portion 12B, a way of dividing into the first straight portion 21 and the second straight portion 22 from the second end portion 12B is not limited. For example, the suture thread 12 and the first straight portion 21 may be formed integrally and the second straight portion 22 may be adhered to the second end portion 12B.

Figure 17:
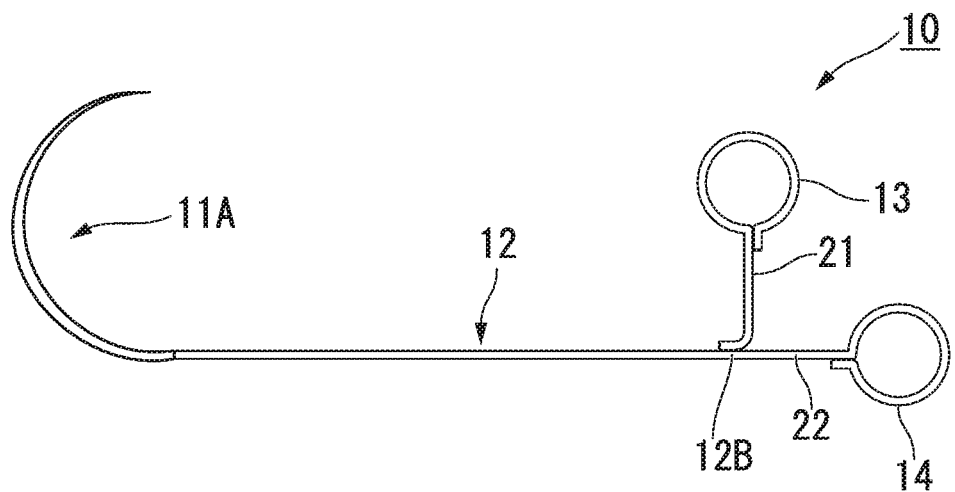
FIG. 17 is an overall view showing another modified example of the suture member of a first embodiment of the present invention.

The shape of the suture needle 11 is not limited and may be a shape according to the suture device. In the laparoscopic surgery and the abdominal surgery, as shown in FIG. 17, a curved needle (suture needle) 11A may be provided instead of a straight suture needle 11.

Furthermore, although the length S1 is longer than the length S2, the length S1 may be same as the length S2. It is preferable that the rigidity of the second loop portion 14 is higher than the rigidity of the first loop portion 13 because eventually the suture thread 12 is passed through the second loop portion 14 and is tightened.

The method for suturing the suture member 10 according to the above present invention may be changed as below.

Modified Example 1 of the Method For Suturing

A modified example 1 of the method for suturing using the suture member 10 according to the present invention will be described with reference to FIGS. 18 and 19.

In the present invention, because a way of passing the suture thread in the step ST4 and the step ST5 is different from the above method for suturing, only this point will be described.

Figure 18:
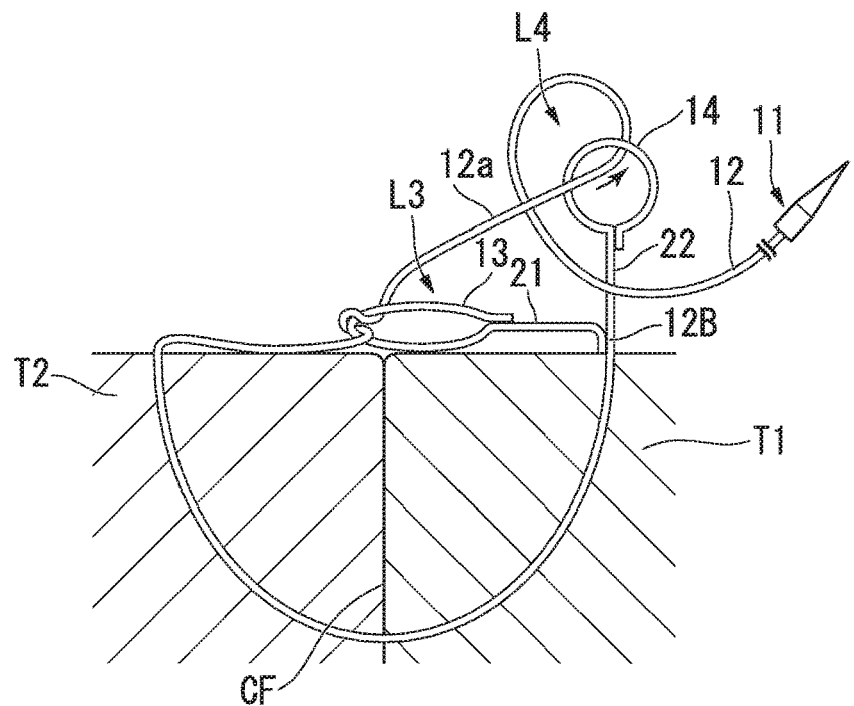
FIG. 18 is a view showing another method for suturing a tissue using the suture member of FIG. 1.

A step ST4 of the modified example, as shown in FIG. 18, the operator passes the suture needle 11 through the second loop portion 14 from the front side of the second loop portion 14 once. The operator causes the suture thread 12 passing through the second loop portion 14 to intersect with the suture thread 12a extending from the first loop portion 13 toward the second loop portion 14 in the back side of the suture thread 12a. The operator passes the suture needle 11 through a loop L3 formed by the first loop portion 13, the suture thread 12a, the second loop portion 14, the first straight portion 21, and the second straight portion 22 from the back side of the loop L3.

Figure 19:
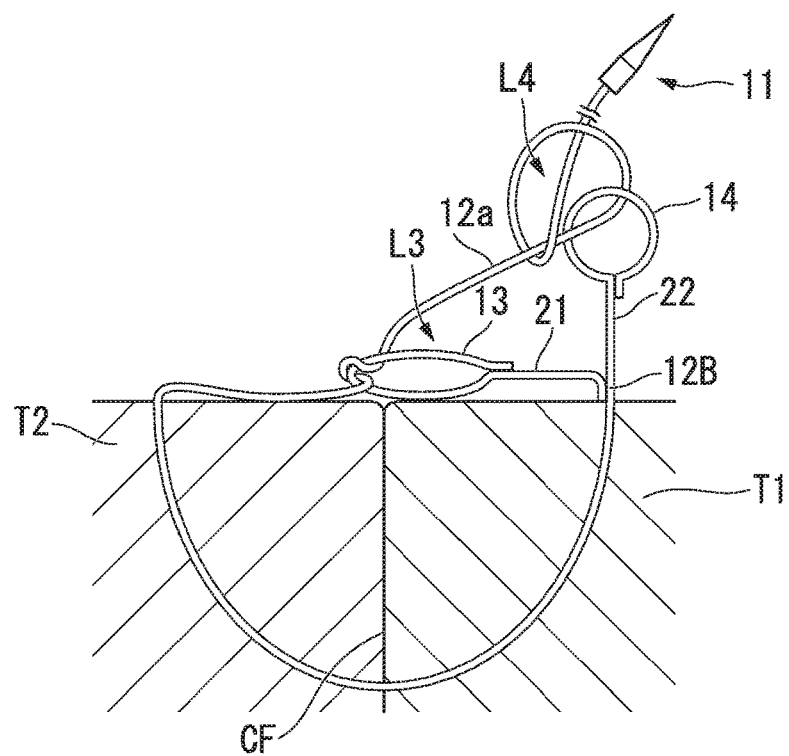
FIG. 19 is a view showing another method for suturing the tissue using the suture member of FIG. 1.

Next, as shown in FIG. 19, the operator passes the suture needle 11 through the loop L4 from the front side (step ST5), the loop L4 being formed by the suture thread 12 passing through the second loop portion 14 and the suture thread 12a that extends from the first loop portion 13 toward the second loop portion 14.

After that, as with the above step ST6, the operator pulls the suture needle 11 toward a direction (arrow A direction) away from the tissue and tightens the suture thread 12. Therefore, the surgical knot is completed.

In this modified example, the same effects as the first embodiment can be obtained.

Modified Example 2 of the Method For Suturing

A modified example 2 of the method for suturing using the suture member 10 according to the present invention will be described with reference to FIGS. 20 and 25.

In the above-mentioned method for suturing, the surgical knot is used. In this modified example, because a "square knot" and a "granny knot" are used, the way of passing the suture thread is different in the step ST2, the step ST4, and the step ST5. This point will be described below.

Figure 20:
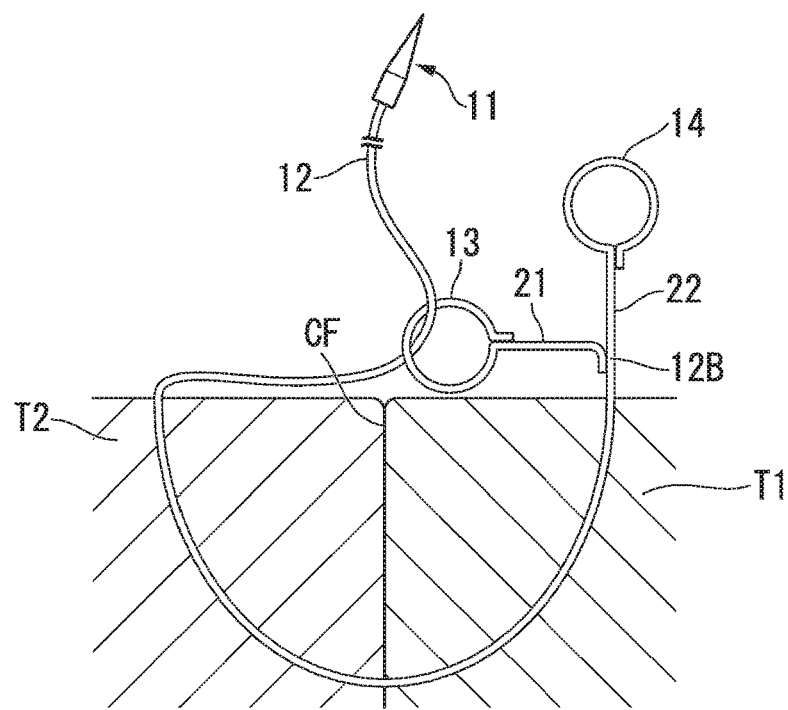
FIG. 20 is a view showing another method for suturing the tissue using the suture member of FIG. 1.

In the step ST2, as shown in FIG. 20, the operator manipulates the first grasping member 31 and the second grasping member 32 (not shown), passes the suture needle 11 through the first loop portion 13 from a back side of the first loop portion 13 once, and causes the suture thread 12 to be entangled in the first loop portion 13.

Figure 21:
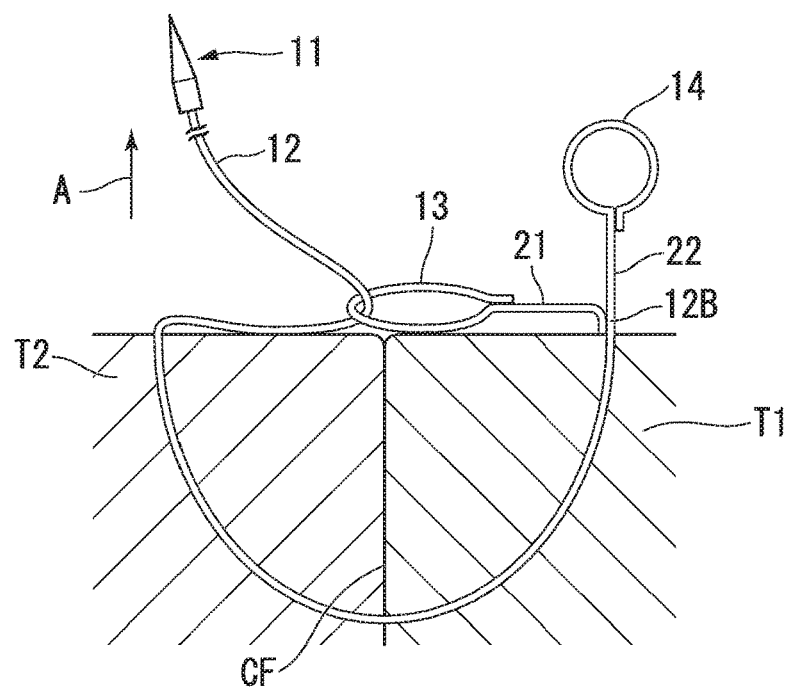
FIG. 21 is a view showing another method for suturing the tissue using the suture member of FIG. 1.

The operator pulls the suture needle 11 toward a direction (arrow A direction) away from the tissue (step ST3: see FIG. 21).

Figure 22:
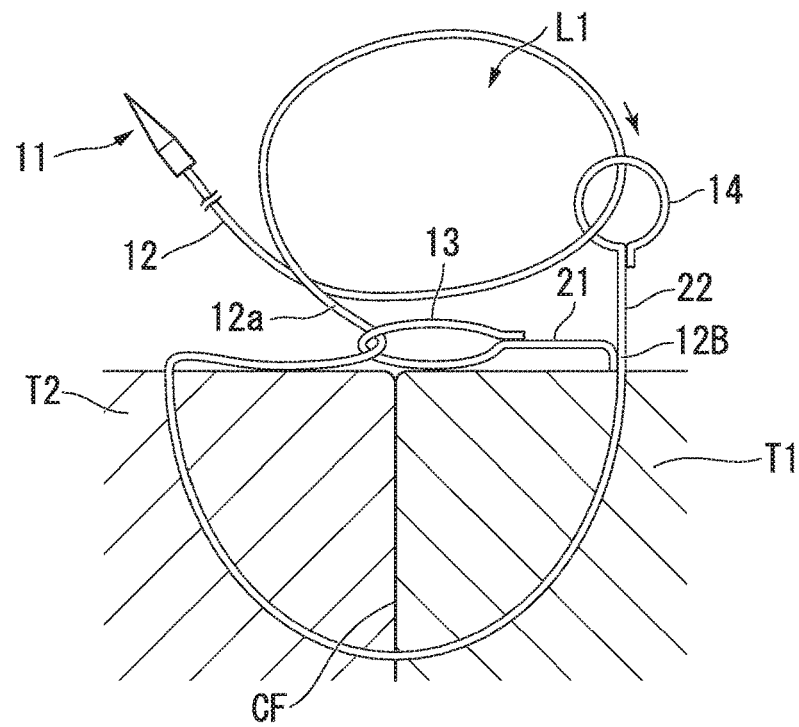
FIG. 22 is a view showing another method for suturing the tissue using the suture member of FIG. 1.

In a case of "square knot", in the step ST4, as shown in FIG. 22, the operator passes the suture needle 11 through the second loop portion 14 from a back side of the second loop portion 14 once, and makes a loop L1 by intersecting the suture thread 12 passing through the second loop portion 14 with the suture thread 12a extending from the first loop portion 13 toward the second loop portion 14 in the back side of the suture thread 12a.

Figure 23:
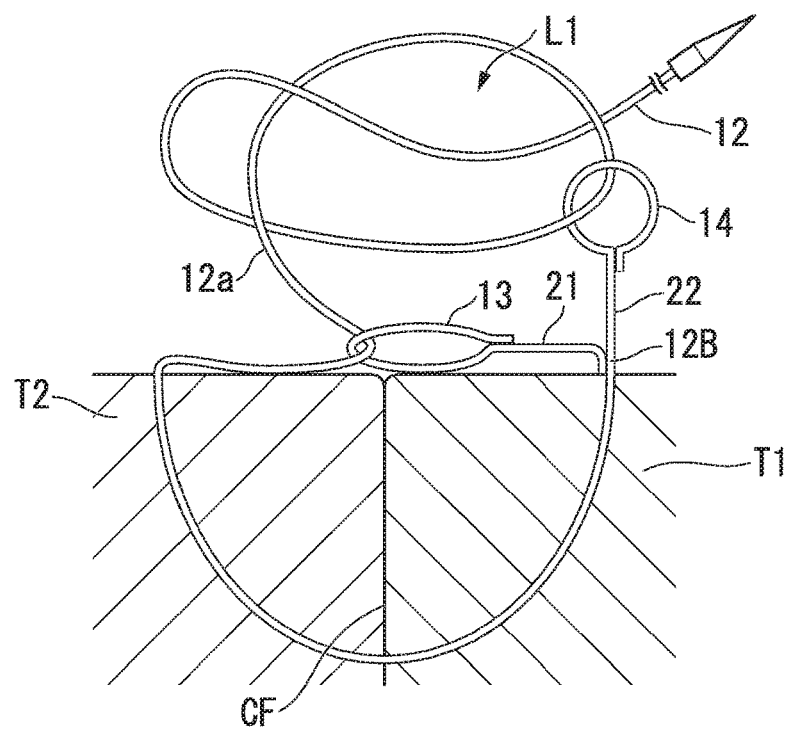
FIG. 23 is a view showing another method for suturing the tissue using the suture member of FIG. 1.

The operator passes the suture needle 11 through the loop L1 from a front side (a direction opposite to a direction in which the suture thread 12 is passed through the second loop portion 14) of the loop L1 once (step ST5: see FIG. 23).

Figure 24:
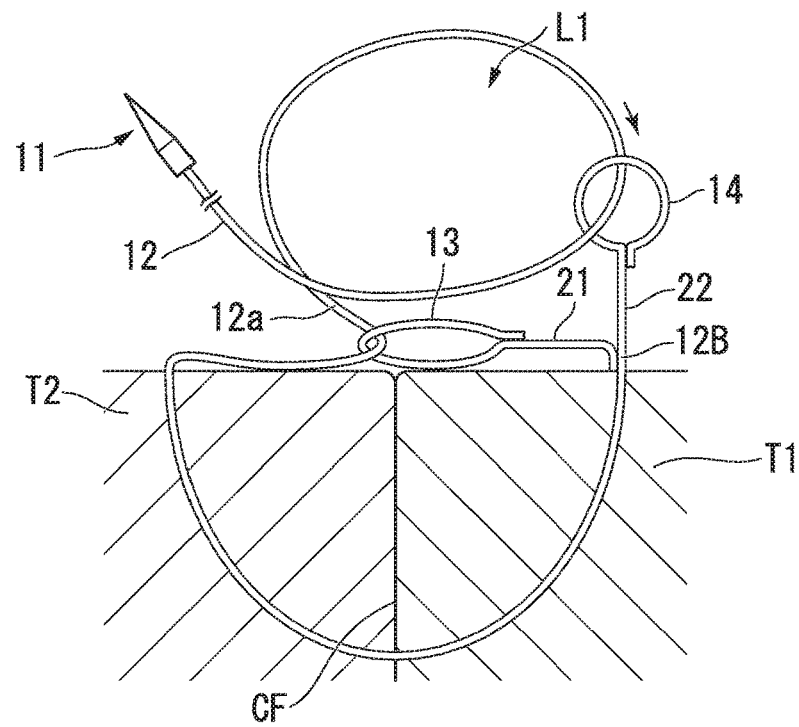
FIG. 24 is a view showing another method for suturing the tissue using the suture member of FIG. 1.

In a case of "granny knot", in the step ST4, as shown in FIG. 24, the operator passes the suture needle 11 through the second loop portion 14 from a back side of the second loop portion 14 once, and makes a loop L1 by intersecting the suture thread 12 passing through the second loop portion 14 with the suture thread 12a extending from the first loop portion 13 toward the second loop portion 14 in the front side (step ST4).

Figure 25:
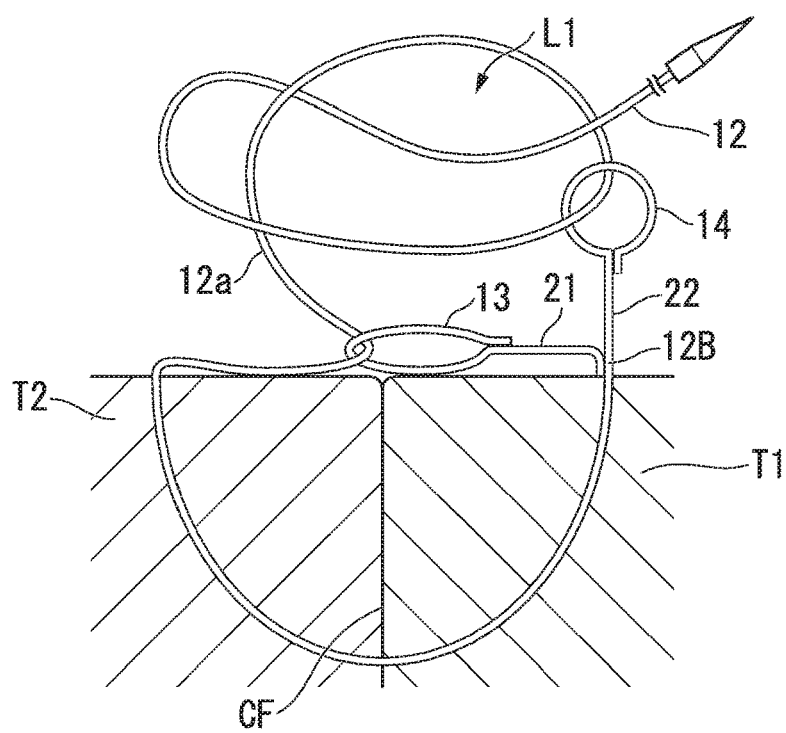
FIG. 25 is a view showing another method for suturing a tissue using the suture member of FIG. 1.

The operator passes the suture needle 11 through the loop L1 from the back side (a direction same as a direction in which the suture thread 12 is passed through the second loop portion 14) of the loop L1 once (step ST5: see FIG. 25).

After that, in any of "square knot" and "granny knot", as with the above step ST6, the operator pulls the suture needle 11 toward a direction (arrow A direction) away from the tissue and tightens the suture thread 12. Therefore, ligation is completed.

As shown in this modified example, the same effects as the method for suturing of the first embodiment can be obtained using any of "square knot" and "granny knot".

Second Embodiment

A suture member of a second embodiment of the present invention will be described with reference to FIGS. 26 and 27.

The suture member 50 of the present embodiment that includes a rubber ring (stopper) 51 is different from the suture member 10 of the first embodiment. The same reference numerals will be given to the equivalent configuration of the suture member 10 of the first embodiment, and the detailed description will be omitted.

Figure 26:
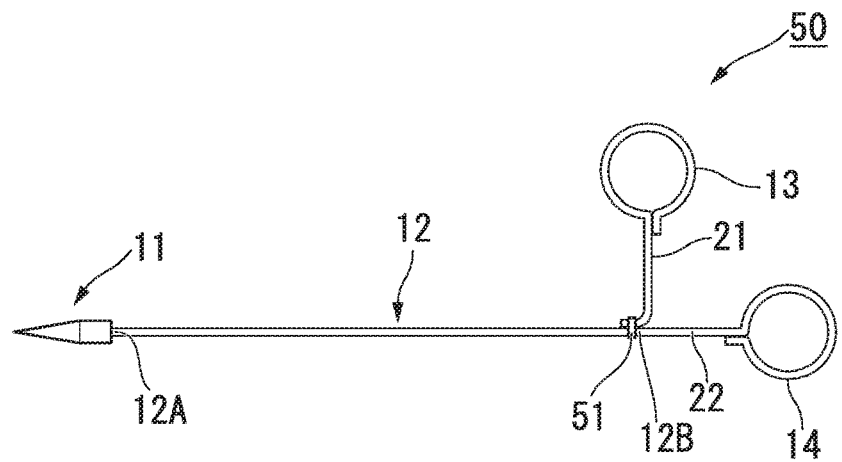
FIG. 26 is an overall view showing a suture member of a second embodiment of the present invention.

The rubber ring (stopper) 51, as shown in FIG. 26, is provided to the second end portion 12B of the suture thread 12. The rubber ring (stopper) 51 is provided so as to cover the first straight portion 21 fixed to the second end portion 12B with the adhesive. The first straight portion 21 does not have to be fixed with the adhesive, but may be fixed by the rubber ring 51.

Figure 27:
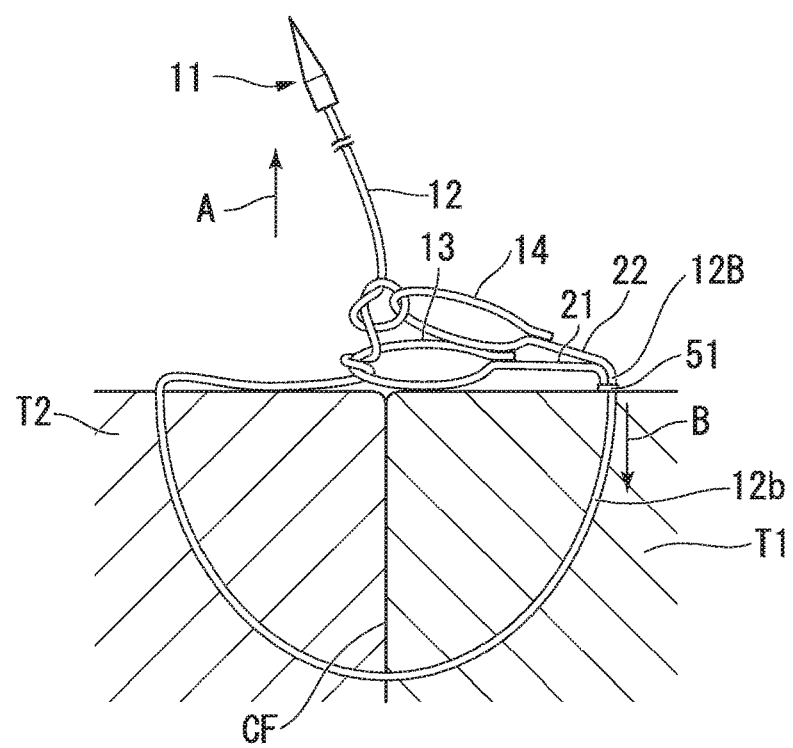
FIG. 27 is a view showing a method for suturing the tissue using the suture member of FIG. 26.

In the step ST2 and the step ST6, when the suture thread 12 is tightened, as shown in FIG. 27, a force may be applied to the suture thread 12b in the first tissue T1 toward an arrow B direction. In this case, the rubber ring 51 serves as a stopper, and prevents the first straight portion 21 and the second straight portion 22 that are arranged at the proximal end side than the rubber ring 51 from being buried in the first tissue T1.

According to the suture member 50 of the present invention, because the rubber ring 51 prevents the first straight portion 21 and the second straight portion 22 from being buried in the first tissue T1, the first loop portion 13 and the second loop portion 14 are definitely positioned on the first tissue T1. Therefore, even if the force is applied to the suture thread 12 more than needed, the suture can be definitely performed.

The rubber ring 51 is marked with a visible marker. The operator uses the marker, while pulling the suture needle 11 or the suture thread 12 to prevent the first loop portion 13 and the second loop portion 14 from being buried in the first tissue T1.

Third Embodiment

A suture member of a third embodiment of the present invention will be described with reference to FIGS. 28 and 29.

The suture member 60 of the present embodiment that includes loops more than three (for example, four loops) is different from the suture member 10 of the first embodiment. The same reference numerals will be given to the equivalent configuration of the suture member 10 of the first embodiment, and a detailed description will be omitted.

Figure 28:
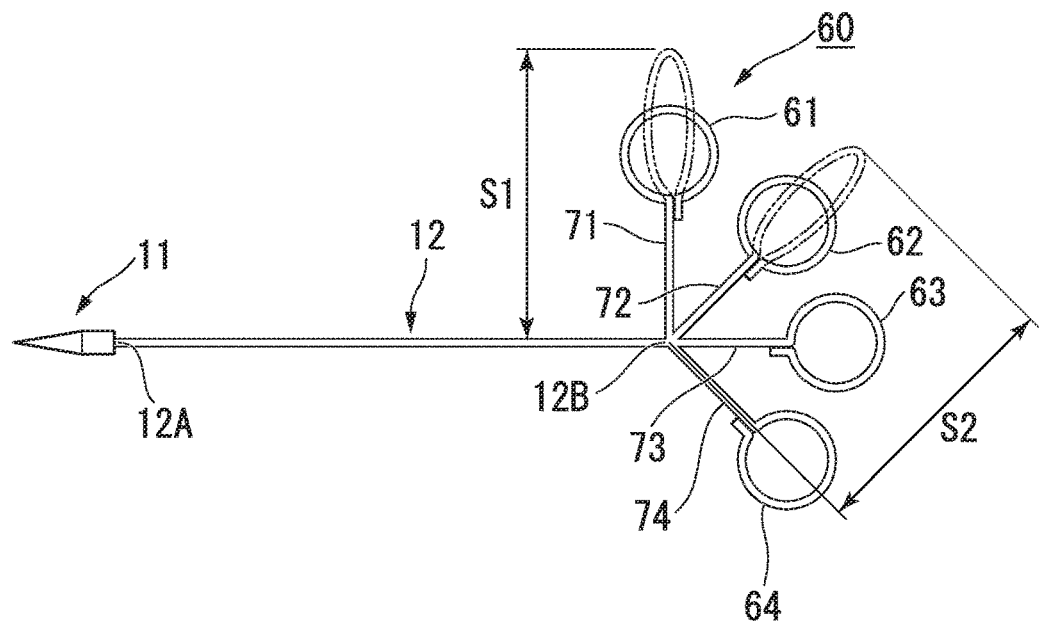
FIG. 28 is an overall view showing a suture member of a third embodiment of the present invention.

As shown in FIG. 28, the suture member 60 of the present invention includes a first loop portion 61, a second loop portion 62, a third loop portion 63, and a fourth loop portion 64 at the second end portion 12B of the suture thread 12.

The suture member 60 includes a first straight portion 71 that is provided between the second end portion 12B and the first loop portion 61, a second straight portion 72 that is provided between the second end portion 12B and the second loop portion 62, a third straight portion 73 that is provided between the second end portion 12B and the third loop portion 63, and a fourth straight portion 74 that is provided between the second end portion 12B and the fourth loop portion 64. That is, the second end portion 12B is a branching point at which the suture thread 12 is divided into the first straight portion 71, the second straight portion 72, the third straight portion 73, and the fourth straight portion 74.

The way of branching is not limited; for example, the suture thread is formed by twisting together a plurality of threads, and the straight portions 71, 72, 73, 74 and the loop portions 61, 62, 63, 64 are formed by untwisting the twisting threads.

The sum of the length of the second straight portion 72 and the maximum length of the second loop portion 62 in a longitudinal direction of the second straight portion 72 is the same as the sum of the length of the third straight portion 73 and the maximum length of the third loop portion 63 in a longitudinal direction of the third straight portion 73, and is the same as the sum of the length of the fourth straight portion 74 and the maximum length of the fourth loop portion 64 in a longitudinal direction of the fourth straight portion 74.

The sum of a length S1 of the first straight portion 71 and the maximum length of the first loop portion 61 in a longitudinal direction of the first straight portion 71 is longer than the length S2.

Next, a method for suturing the body tissue by the suture device using the suture member will be described.

In the present invention, because a way of passing the suture thread 12 through the loop portion is same as the first embodiment, only the order of passing the suture thread 12 through the loop portion that is different from the first embodiment will be described.

First, the operator passes the suture needle 11 through the first loop portion 61 twice. Next, the operator passes the suture needle 11 through the second loop portion 62 once. After that, the operator performs the steps ST3, ST4, and ST5 that are same as the first embodiment. Next, the operator passes the suture needle 11 through the third loop portion 63 once. After that, the operator performs the steps ST3, ST4, and ST5 that are same as those of the first embodiment. Next, the operator passes the suture needle 11 through the fourth loop portion 64 once. After that, the operator performs the steps ST3, ST4, and ST5 that are the same as those of the first embodiment. In this way, the suture of the tissues is completed.

In the present embodiment, because the suture member 60 includes the second loop portion 62, the third loop portion 63, and the fourth loop portion 64, the suture thread 12 is tightened using the step ST5 three times. Therefore, when the operator wants to increase a number of a knot, the suture member 60 can be used effectively.

Figure 29:
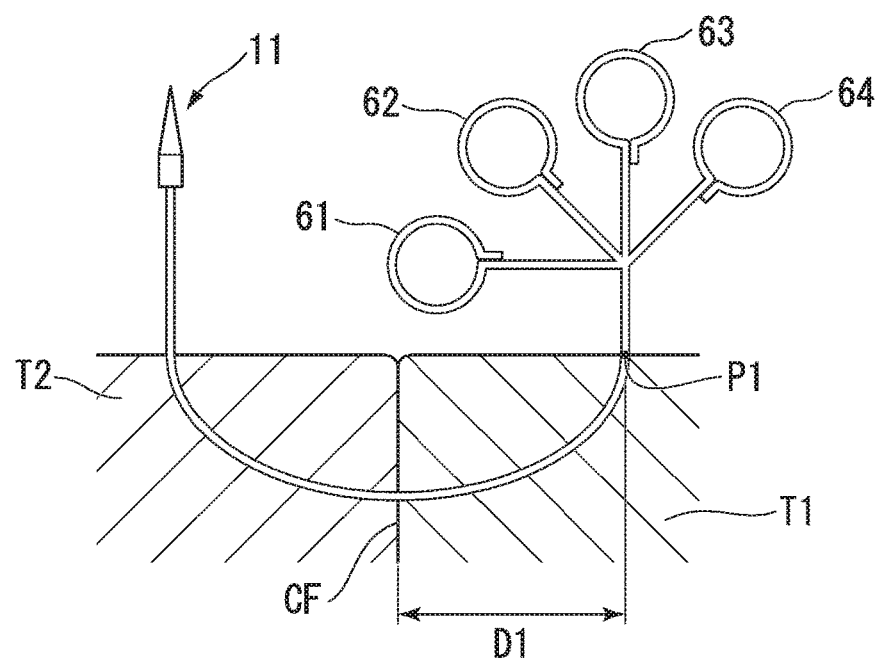
FIG. 29 is a view showing a method for suturing the tissue using the suture member of FIG. 28.

Furthermore, as shown in FIG. 29, in the case where the operator sutures the tissue shallowly, the operator wants a position at which the piercing point P1 is close to the contact face CF compared to suture the tissue deeply. In this case, because the suture thread 12 is divided into the loop portions 61, 62, 63, 64 from the second end portion 12B, even if the piercing point P1 is close to the contact face CF, a distance D1 is longer than the length S1. Therefore, when the operator wants to suture the tissue shallowly, the suture member 60 can be used effectively.

Modified Example

Figure 30:
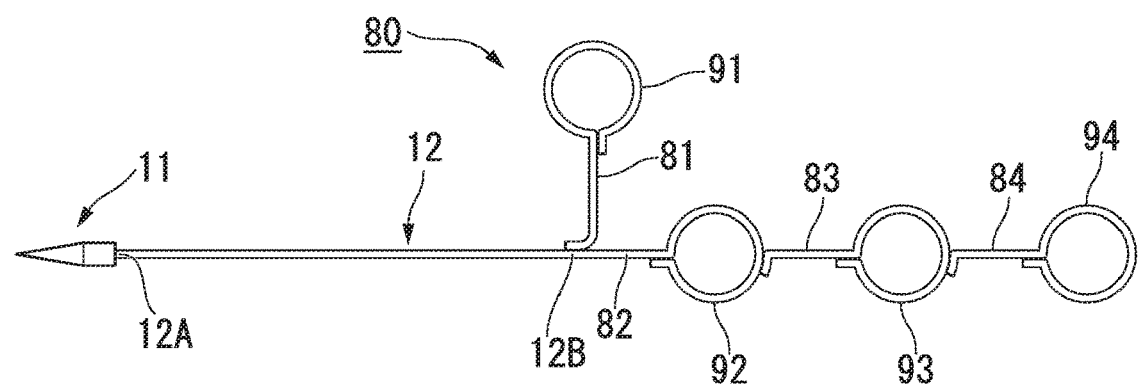
FIG. 30 is an overall view showing a modified example of the suture member of the third embodiment of the present invention.

A suture member of a modified example of this embodiment will be described with reference to FIGS. 30 and 31.

In a suture member 80 of the modified example, because positions of a first loop portion 91, a second loop portion 92, a third loop portion 93, and a fourth loop portion 94 are different from the suture member 60 of the third embodiment, only this point will be described.

In a suture member 80, the suture thread 12 is divided into the first straight portion 81 and the first loop portion 91, and the second straight portion 82 and the second loop portion 92 from the second end portion 12B. The third straight portion 83 and the third loop portion 93, and the fourth straight portion 84 and the fourth loop portion 94 are arranged in this order.

The third straight portion 83 is fixed to the second loop portion 92 with an adhesive. The fourth straight portion 84 is fixed to the third loop portion 93 with an adhesive. The way of fixing the third straight portion 83 and the fourth straight portion 84 is not limited, the third straight portion 83 may be wound around the second loop portion 92. The third straight portion 84 may be wound around the third loop portion 93.

As with the third embodiment, first of all, the order of passing the suture thread 12 through the loop portion, the operator passes the suture needle 11 through the first loop portion 91 twice, and passes the suture needle 11 through the second loop portion 92 once. After that, the operator performs the steps ST3, ST4, and ST5 that are same as the first embodiment. Next, the operator passes the suture needle 11 through the third loop portion 93 once. After that, the operator performs the steps ST3, ST4, and ST5 that are same as the first embodiment. Next, the operator passes the suture needle 11 through the fourth loop portion 94 once. After that, the operator performs the steps ST3, ST4, and ST5 that are same as the first embodiment.

In the present embodiment, because the suture member 80 includes the second loop portion 92, the third loop portion 93, and the fourth loop portion 94, the suture thread 12 is tightened using the step ST5 three times. Therefore, when the operator wants to increase a number of a knot, the suture member 60 can be used effectively.

Figure 31:
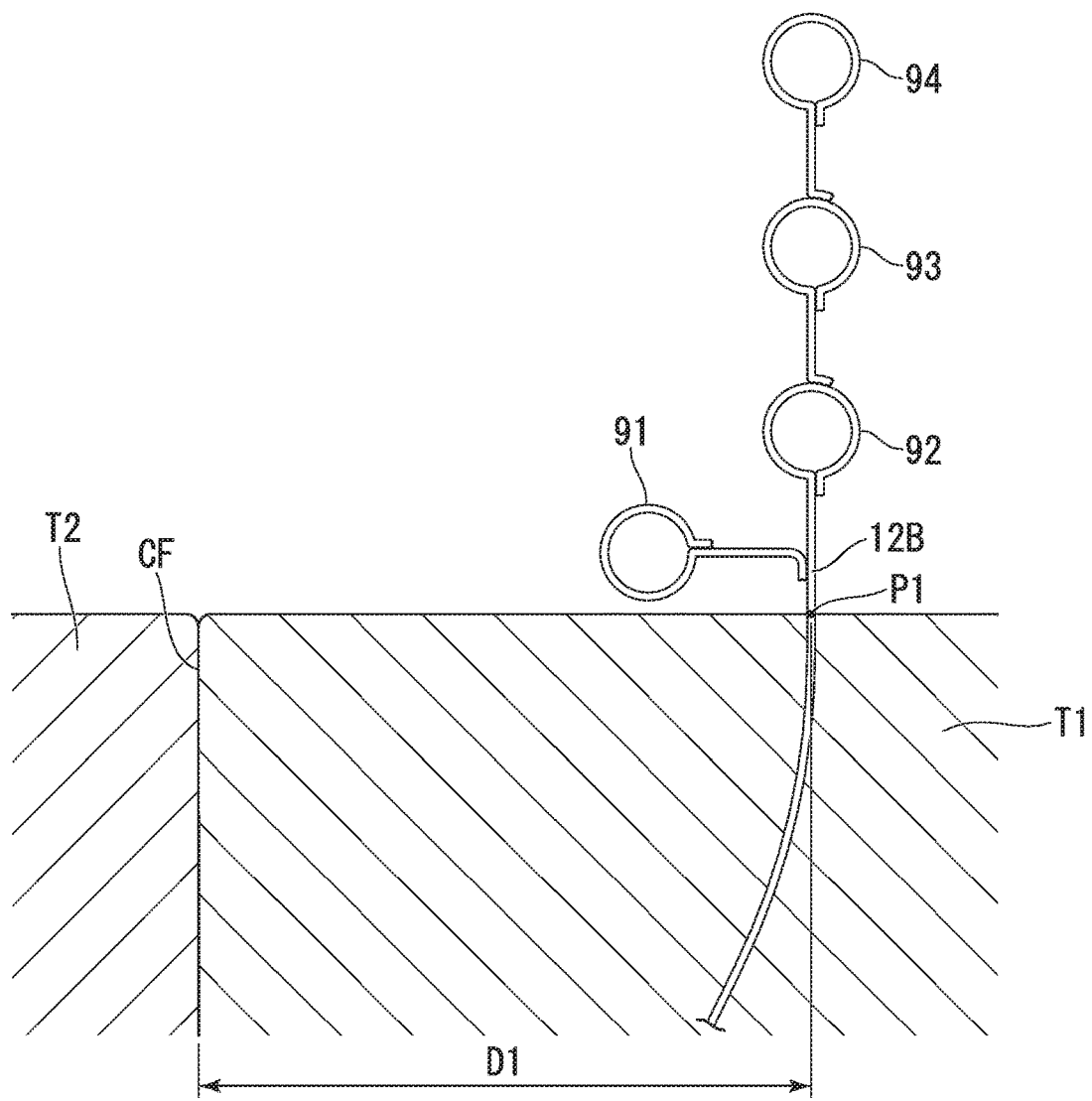
FIG. 31 is a view showing a method for suturing the tissue using the suture member of FIG. 30.

Furthermore, as shown in FIG. 31, in the case where the operator sutures the tissue deeply, the operator wants a position at which the piercing point P1 is away from the contact face CF compared to suture the tissue shallowly. In this case, even if the piercing point P1 is away from the contact face CF, the fourth loop portion 94 is positioned on or over the contact face CF because the second loop portion 92, the third loop portion 93, and the fourth loop portion 94 are connected tandemly. Therefore, it is possible to apply a desired tension to the first tissue T1 and the second tissue T2.

While the preferred embodiments of the invention have been described and shown above, it should be understood that these are exemplary of the invention and are not to be considered as limiting. Additions, omissions, substitutions, and other modifications of components can be made without departing from the concept of the invention. The present invention is not limited by the description above, and it is limited by the scope of the appended claims.

What is claimed is:

1. A suture member that sutures a tissue, the suture member comprising;
   a suture needle of which a distal end is sharp;
   a suture thread which includes a first end portion and a second end portion, of which the first end portion is connected to the suture needle, and which sutures the tissue;
   a first loop portion which has a ring shape, through which the suture needle is capable of passing, and which is connected to the second end portion;
   a second loop portion which has a ring shape, through which the suture needle is capable of passing, which is connected to the second end portion, and which is separated from the first loop portion;
   a first straight portion which is provided between the second end portion and the first loop portion; and
   a second straight portion which is provided between the second end portion and the second loop portion.

2. The suture member according to claim 1, wherein
   a sum of a length of the first straight portion and a maximum length of the first loop portion in a longitudinal direction of the first straight portion is larger than a sum of a length of the second straight portion and a maximum length of the second loop portion in a longitudinal direction of the second straight portion.

3. The suture member according to claim 1, wherein
   a stopper that prevents the first loop portion and the second loop portion from being buried in the tissue is provided to the second end portion.

4. The suture member according to claim 1, wherein
   a visible marker is provided in the second end portion.

5. A method for suturing a first tissue and a second tissue by a suture device using the suture member according to claim 1, the method comprising:
   causing the suture needle to penetrate from the first tissue through the second tissue and protruding the suture needle and the suture thread from the second tissue side;
   passing the suture needle through the first loop portion from a back side thereof twice, and entangling the suture thread in the first loop portion by manipulating the suture device;
   pulling the suture needle toward a direction away from the first tissue and the second tissue, and tightening the suture thread;
   making a loop by intersecting the suture thread passing through the second loop portion with the suture thread extending from the first loop portion toward the second loop portion in the back side of the suture thread extending from the first loop portion toward the second loop portion;
   passing the suture needle through the loop from a front side of the loop once by manipulating the suture device; and
   pulling the suture needle toward a direction away from the first tissue and the second tissue, and tightening the suture thread.

* * * * *